(12) United States Patent
Sun et al.

(10) Patent No.: US 9,586,194 B2
(45) Date of Patent: Mar. 7, 2017

(54) PROCESS AND CATALYST FOR CONVERSION OF ACETIC ACID TO ISOBUTENE

(71) Applicants: Archer Daniels Midland Company, Decatur, IL (US); Washington State University, Pullman, WA (US)

(72) Inventors: Junming Sun, Pullman, WA (US); Changjun Liu, Pullman, WA (US); Yong Wang, Pullman, WA (US); Kevin Martin, Mt. Zion, IL (US); Padmesh Venkitasubramanian, Forsyth, IL (US)

(73) Assignee: Washington State University, Pullman, WA (US)

( * ) Notice: Subject to any disclaimer, the term of this patent is extended or adjusted under 35 U.S.C. 154(b) by 55 days.

(21) Appl. No.: 14/683,175

(22) Filed: Apr. 10, 2015

(65) Prior Publication Data
US 2015/0239799 A1     Aug. 27, 2015

Related U.S. Application Data

(63) Continuation of application No. PCT/US2013/062784, filed on Oct. 1, 2013, and a
(Continued)

(51) Int. Cl.
*C07C 1/00* (2006.01)
*C07C 1/20* (2006.01)
(Continued)

(52) U.S. Cl.
CPC ............ *B01J 23/06* (2013.01); *B01J 37/04* (2013.01); *B01J 37/08* (2013.01); *C07C 1/2072* (2013.01);
(Continued)

(58) Field of Classification Search
CPC ..................... C07C 1/2078; C07C 2523/06
See application file for complete search history.

(56) References Cited

U.S. PATENT DOCUMENTS

| | | | | |
|---|---|---|---|---|
| 4,935,360 A | * | 6/1990 | Klemps | C12P 7/54 435/140 |
| 7,005,541 B2 | * | 2/2006 | Cheung | C07C 51/12 562/519 |

(Continued)

OTHER PUBLICATIONS

Sun et al., Jun. 2011, Direct conversion of bio-ethanol to isobutene on nanosized ZnxZryOz mixed oxides with balanced acid-base sites, JACS, vol. 133, pp. 11096-11099.*

*Primary Examiner* — In Suk Bullock
*Assistant Examiner* — Youngsul Jeong
(74) *Attorney, Agent, or Firm* — William B. Miller

(57) ABSTRACT

A process is disclosed for converting acetic acid to isobutene in the presence of a catalyst. In certain embodiments, a $Zn_xZr_yO_z$ mixed oxide catalyst is used for carrying out a gas phase process for converting acetic acid to isobutene. In some embodiments, a $Zn_xZr_yO_z$ mixed oxide catalyst made by an incipient wetness impregnation method is used and is indicated to be very stable for carrying out the conversion.

14 Claims, 2 Drawing Sheets

Related U.S. Application Data continuation of application No. PCT/US2013/063968, filed on Oct. 9, 2013.

(60) Provisional application No. 61/720,433, filed on Oct. 31, 2012, provisional application No. 61/737,312, filed on Dec. 14, 2012.

(51) Int. Cl.
*B01J 23/06* (2006.01)
*C07C 5/48* (2006.01)
*B01J 37/04* (2006.01)
*B01J 37/08* (2006.01)
*C07C 45/52* (2006.01)
*C07C 51/235* (2006.01)
*C07C 1/207* (2006.01)

(52) U.S. Cl.
CPC ............. *C07C 5/48* (2013.01); *C07C 45/52* (2013.01); *C07C 51/235* (2013.01); *C07C 2521/06* (2013.01); *C07C 2523/06* (2013.01)

(56) References Cited

U.S. PATENT DOCUMENTS

2006/0161035 A1* 7/2006 Kalnes .................. C07C 1/20
 585/639
2013/0237618 A1* 9/2013 Matsushita ............ B01J 23/80
 518/713

\* cited by examiner

PROCESS AND CATALYST FOR CONVERSION OF ACETIC ACID TO ISOBUTENE

CROSS-REFERENCE TO RELATED APPLICATIONS

The present application is a continuation of International Application No. PCT/US2013/063968 filed Oct. 9, 2013, now published as WO 2014/092849, which directly claims the benefit of U.S. Provisional Application Ser. No. 61/737,312 filed Dec. 14, 2012; and the present application is also a continuation of International Application No. PCT/US2013/062784 filed Oct. 1, 2013, now published as WO 2014/070354, which directly claims the benefit of U.S. Provisional Application Ser. No. 61/720,433 filed Oct. 31, 2012.

TECHNICAL FIELD

The present invention relates generally to renewable process alternatives for the production of isobutene and to the catalysts used therein, but concerns the novel production of isobutene from acetic acid rather than from ethanol.

BACKGROUND ART

Isobutene is widely used for the production of a variety of industrially important products, such as butyl rubber for example. Isobutene has been produced commercially to date through the catalytic or steam cracking of fossil feedstocks, and the development of a commercially viable process for the manufacture of isobutene from a renewable source-based feedstock would accordingly be of great interest as fossil resources are depleted and/or become more costly to use—especially in consideration of increased demand for isobutene.

Previous to the referenced application, a hard-template method had been described for synthesizing $Zn_xZr_yO_z$ mixed oxides for the direct and high yield conversion of ethanol (from the fermentation of carbohydrates from renewable source materials, including biomass) to isobutene, wherein ZnO was added to $ZrO_2$ to selectively passivate zirconia's strong Lewis acidic sites and weaken Brönsted acidic sites while simultaneously introducing basicity. The objectives of the hard template method were to suppress ethanol dehydration and acetone polymerization, while enabling a surface basic site-catalyzed ethanol dehydrogenation to acetaldehyde, an acetaldehyde to acetone conversion via aldol-condensation/dehydrogenation, and a Brönsted and Lewis acidic/basic site-catalyzed acetone-to-isobutene reaction pathway.

High isobutene yields were in fact realized, but unfortunately, as later experienced by Mizuno et al. (Mizuno et al., "One—path and Selective Conversion of Ethanol to Propene on Scandium-modified Indium Oxide Catalysts", Chem. Lett., vol. 41, pp. 892-894 (2012)) in their efforts to produce propylene from ethanol, it was found that further improvements in the catalyst's stability were needed.

The prior, related application concerns the discovery that these improvements could be realized without adding modifying metals and without a reduction in the initial high activity (100 percent ethanol conversion) that had been observed in these mixed oxide catalysts.

SUMMARY OF THE INVENTION

The present invention concerns the discovery that the mixed oxide catalysts we have been evaluating for converting ethanol to isobutene are also able to catalyze the conversion of acetic acid to isobutene. Since acetic acid can be made by a variety of methods from a number of different starting materials, including through carbonylation of methanol derived from sequestered carbon dioxide, for example, the capability of these mixed oxide catalysts to catalyze the conversion of acetic acid to isobutene enables a number of improvements to be realized and a range of options for utilizing renewable resources more efficiently, all as described in greater detail hereafter.

Accordingly, in its broadest aspect, the present invention concerns a process for converting acetic acid to isobutene in the presence of a catalyst.

In another more particular aspect, the catalyst is a mixed oxide catalyst of the formula $Zn_xZr_yO_z$.

In another aspect, the catalyst is an improved stability mixed oxide catalyst of the formula $Zn_xZr_yO_z$, as made by the process of our related application.

In other more particular aspects, the present invention concerns certain integrated processes wherein the inventive step of converting acetic acid to isobutene in the presence of a catalyst is incorporated to enable a plurality of biobased products to be made inclusive of isobutene and/or for improved renewable resource utilization.

DESCRIPTION OF EMBODIMENTS

Figure 1:
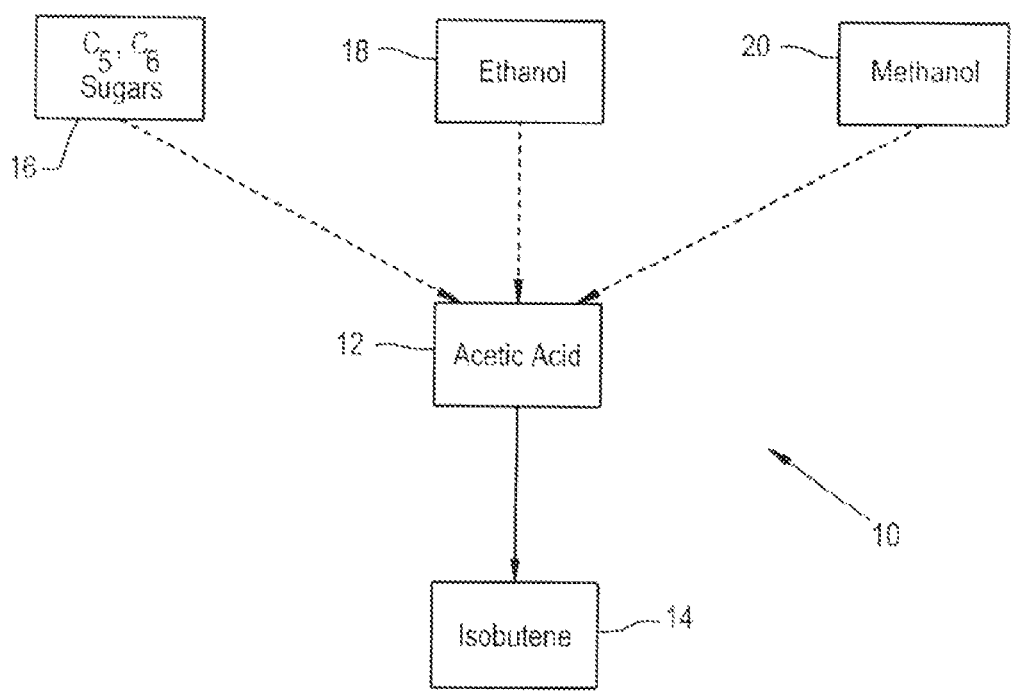
FIG. 1 schematically depicts a process of converting acetic acid to isobutene in the presence of a catalyst, wherein various options for obtaining the acetic acid are suggested.

Referring now to FIG. 1, a process 10 is schematically illustrated wherein acetic acid 12 is converted to isobutene 14 in the presence of a catalyst, particularly, a $Zn_xZr_yO_z$ mixed oxide catalyst.

In one embodiment, the $Zn_xZr_yO_z$ mixed oxide catalyst can be made by a "hard template" or "confined space synthesis" method generally of the character used by Jacobsen et al., "Mesoporous Zeolite Single Crystals", Journal of the American Chemical Society, vol. 122, pp. 7116-7117 (2000), wherein nanozeolites were prepared.

More particularly, the same carbon black (BP 2000, Cabot Corp.) may be used as a hard template for the synthesis of nanosized $Zn_xZr_yO_z$ mixed oxides, rather than nanozeolites as in Jacobsen et al. Prior to use, the BP 2000 template is dried, for example, at 180° C. overnight. Calculated amounts of zirconyl nitrate hydrate (Sigma-Aldrich, greater than 99.8% purity) and $Zn(NO_3)_2 \cdot 6H_2O$ (Sigma-Aldrich, greater than 99.8% purity) are dissolved in a given amount of water, and sonicated for 15 minutes to produce a clear solution with desired concentrations of Zn and Zr. In one preparation, about 25 grams of the obtained solution are then mixed with 6.0 grams of the preheated BP 2000 to achieve incipient wetness, and the mixture is transferred to a ceramic crucible and calcined at 400 degrees Celsius for 4 hours, followed by ramping the temperature to 550 degrees Celsius (at a ramp rate of 3 degrees Celsius/minute) and holding at 550 degrees Celsius for another 20 hours. Nanosized white powders are obtained, having a mean particle size of less than 10 nanometers.

The nanosized $Zn_xZr_yO_z$ mixed oxide catalysts made by a hard template method are further described in Sun et al., "Direct Conversion of Bio-ethanol to Isobutene on Nano-sized $Zn_xZr_yO_z$ Mixed Oxides with Balanced Acid-Base Sites", Journal of the American Chemical Society, vol. 133, pp 11096-11099 (2011), along with findings related to the character of the mixed oxide catalysts formed thereby and the performance of the catalysts for the ethanol to isobutene conversion, given certain Zn/Zr ratios, residence times and reaction temperatures.

Alternatively, the $Zn_xZr_yO_z$ mixed oxide catalysts may be made as described in copending U.S. Patent Application Ser. No. 61/720,433, filed Oct. 31, 2012 for "Stable Mixed Oxide Catalysts for Direct Conversion of Ethanol to Isobutene and Process for Making", by a process broadly comprising, in certain embodiments, forming a solution of one or more Zn compounds, combining one or more zirconium-containing solids with the solution of one or more Zn compounds so that the solution wets the zirconium-containing solids to a state of incipient wetness, drying the wetted solids, then calcining the dried solids. In other embodiments, a solution is formed of one or more Zr compounds, the solution is combined with one or more Zn-containing solids so that the solution wets the Zn-containing solids to a state of incipient wetness, the wetted solids are dried and then the dried solids are calcined.

In certain embodiments, the $Zn_xZr_yO_z$ mixed oxide catalysts (whether made by the hard template or incipient wetness methods) are characterized by a Zn/Zr ratio (x:y) of from 1:100 to 10:1, preferably from 1:30 to 1:1, especially 1:20 to 1:5, and still more preferably 1:12 to 1:10.

Parenthetically, in the present application where any range of values is given for any aspect or feature of the catalysts of the present invention or any process described for using the catalysts of the present invention, the given ranges will be understood as disclosing and describing all subranges of values included within the broader range. Thus, for example, the range of 1:100 to 10:1 will be understood as disclosing and describing not only the specific preferred and more preferred subranges given above, but also every other subrange including a value for x between 1 and 10 and every other subrange including a value for y between 1 and 100.

The catalysts made by the alternative, incipient wetness method are consistent in their particle size with the catalysts described in the journal article, namely, comprising aggregates of less than 10 nm-sized particles with a highly crystalline structure. The Zn oxide component is again highly dispersed on the Zr oxide component.

In certain embodiments, the $Zn_xZr_yO_z$ mixed oxide catalysts are characterized as low sulfur catalysts, containing less than 0.14 percent by weight of sulfur. In the related copending application, it was reported in this regard that catalysts made by the incipient wetness method would desirably be substantially sulfur-free, preferably including less than 0.01 percent by weight of sulfur and more preferably including less than 0.001 weight percent of sulfur. In the prior related application, it was postulated that the reduced sulfur content enabled by the incipient wetness method as compared to the hard template method contributed significantly to the much improved stability observed for the incipient wetness method catalysts of the prior related application for the ethanol to isobutene process.

In the present context of a process for converting acetic acid to isobutene, however, in at least some embodiments and under certain process conditions some sulfur does appear to be beneficial, though as just indicated, it is expected that the amount of sulfur will preferably be such that the catalysts are characterized as low sulfur catalysts. Such low sulfur catalysts are most readily made by the incipient wetness method described briefly above and in greater detail in the prior related application.

In principle, provided the zinc and zirconium compounds and solids in these embodiments have a sufficiently low sulfur content in order to produce a low sulfur content when combined according to the incipient wetness method, any combination of zinc and zirconium materials and any solvent can be used that will permit the zinc and zirconium components to mix homogeneously whereby, through incipient wetness impregnation, one of the zinc or zirconium components are well dispersed on a solid of the other component for subsequent drying and conversion to the oxide forms through calcining. As exemplified below, low sulfur catalysts can also be made by the incipient wetness method starting with zinc and zirconium compounds that are sulfur-free or substantially sulfur-free, then doping in a desired sulfur content into the $Zn_xZr_yO_z$ mixed oxide catalysts used in certain embodiments of the inventive process.

The conditions and times for the drying and calcining steps of an incipient wetness preparation will depend, of course, on the particular zinc and zirconium materials and solvent used, but in general terms, the drying step can be accomplished in a temperature range of from 60 degrees Celsius to 200 degrees Celsius over at least 3 hours, while the calcining can take place at a temperature of from 300 degrees Celsius to 1500 degrees Celsius, but more preferably a temperature of from 400 to 600 degrees Celsius is used. The calcination time can be from 10 minutes to 48 hours, with from 2 to 10 hours being preferred.

In still other embodiments, low sulfur catalysts as described herein could be prepared by a hard template method as described in the earlier incorporated publication, except that a suitably very low sulfur content carbon is used for the hard template to realize a low sulfur content in the finished catalyst.

In certain embodiments, the process can be conducted continuously in the gas phase, using a fixed bed reactor or flow bed reactor. The reaction temperature may be in a range from 350 to 700 degrees Celsius, preferably, in a range from 400 to 500 degrees Celsius, and the WHSV can be in a range from $0.01\ hr^{-1}$ to $10\ hr^{-1}$, preferably from $0.05\ hr^{-1}$ to $2\ hr^{-1}$. Acetic acid/water solutions with steam to carbon ratios from 0 to 20, preferably from 2 to 5 can be used to provide acetic acid to the catalyst. An inert carrier gas, such as nitrogen, can be used as in Example 1.

As shown schematically in FIG. 1, the acetic acid 12 can be obtained by various methods from a number of starting materials, which in turn permits a number of integrated processes to be considered for producing other products in addition to isobutene and/or for providing improved utilization of renewable resources.

For example, acetic acid can be produced from a source of five and six carbon sugars 16 by fermentation. U.S. Pat. Nos. 6,509,180 and 8,252,567 seek to improve upon known processes for making ethanol and butanol/hexanol, respectively, by means including the fermentation of five and six carbon sugars into acetic acid. In U.S. Pat. No. 6,509,180, the acetic acid is esterified to form an acetate ester which may then be hydrogenated (using hydrogen from, e.g., steam reforming of natural gas, electrolysis of water, gasification of biomass or partial oxidation of hydrocarbons generally) to ethanol. In U.S. Pat. No. 8,252,567, the ethanol formed in this manner can be used to make butanol and hexanol, by subjecting the ethanol with acetate, acetic acid or mixtures thereof to an acidogenic fermentation using, for example, species of the bacteria *Clostridium* (*Clostridium kluyveri* is mentioned), to produce butyrate, butyric acid, caproate, caproic acid or mixtures thereof. These materials then in turn are acidified to convert butyrate and caproate to butyric acid and caproic acid, the butyric and caproic acids are esterified and then the butyric and caproic acid esters undergo reduction by hydrogenation, hydrogenolysis or reduction by carbon monoxide to provide butanol and ethanol.

As related in these two patents and as well known to those skilled in the fermentation art, the fermentation of five and six carbon sugars to form acetic acid can be accomplished by various organisms. More particularly, homoacetogenic microorganisms are able through fermentation to produce acetic acid with 100% carbon yield; these microorganisms internally convert carbon dioxide to acetate, in contrast to a process for producing ethanol from sugars obtained from biomass (the starting point for isobutene syntheses reported in the prior related application and in the earlier journal article (Sun et al., "Direct Conversion of Bio-ethanol to Isobutene on Nanosized $Zn_xZr_yO_z$ Mixed Oxides with Balanced Acid-Base Sites", Journal of the American Chemical Society, vol. 133, pp 11096-11099 (2011)) wherein carbon dioxide is produced as a byproduct.

Examples of homoacetogens given by U.S. Pat. No. 8,252,567 are microorganisms of the genus *Moorella* and *Clostridium*, especially microorganisms of the species *Moorella thermoaceticum* (described as formerly classified as *Clostridium thermoaceticum*) or *Clostridium formicoaceticum*. U.S. Pat. No. 8,252,567 represents that about one hundred known acetogens in twenty-two genera were known as of 2009, and cross-references Drake, et al., Ann. NY Acad. Sci. 1125: 100-128 (2008) for a review of acetogenic microorganisms.

Other references describing fermentation methods for producing acetic acid from five and six carbon sugars include U.S. Pat. Nos. 4,935,360; 8,236,534; 4,513,084; 4,371,619 and 4,506,012; both one-step fermentation processes from the sugars to acetic acid, acetates or both are disclosed, as well as two-step processes involving a first fermentation to lactic acid (by *lactobacillus* or known methods of homolactic fermentation, preferably) followed by a second fermentation to convert lactic acid to acetic acid, for example, using *Clostridium formicoaceticum*.

Any of the known fermentation methods may, in short, be used to produce acetic acid for conversion to isobutene in the presence of the mixed oxide catalysts of the present invention, but homoacetogenic fermentation methods are considered preferable in that carbon dioxide is not produced as a byproduct—the carbon dioxide represents a yield loss from the overall process to make isobutene and as a greenhouse gas is undesirable particularly in the context of a process to make a needed product more sustainably from renewable resources.

As well or in the alternative, the acetic acid feedstock 12 can be made from ethanol 18, according to any of several known methods employing oxidative fermentation with acetic acid bacteria of the genus *Acetobacter*.

As well or in the alternative, the acetic acid feedstock 12 can be made from methanol 20 through combination with carbon monoxide according to the most industrially used route for making acetic acid, for example, in the presence of a catalyst under conditions effective for the carbonylation of methanol. A variety of carbonylation catalysts are known in this regard, see, for example, U.S. Pat. Nos. 5,672,743; 5,728,871; 5,773,642; 5,883,289; 5,883,295.

Those skilled in the art will appreciate that making at least a portion of the acetic acid feedstock 12 from methanol 20 would enable other integrated process options to be considered for making isobutene from a biomass. Thus, syngas may be produced by gasification of a biomass, and methanol then produced from the syngas with additional hydrogen provided, for example, through electrolysis of water. The electrical energy required for the electrolysis may in turn be generated from combustion of additional biomass, through steam from heat energy captured from the methanol synthesis or from combustion of a biomass fraction (lignin, for example), with optional capture and recycle of carbon dioxide from the flue gas to be used in the methanol synthesis. A variety of options for producing methanol from biomass have been presented in the literature, see, for example, US 2007/0254969 A1 by Olah et al; U.S. Pat. Nos. 6,645,442 and 6,991,769, both by Kaneko et al; and U.S. Pat. No. 6,340,581 to Gaddy.

Those skilled in the art will appreciate that still other options may be considered for producing acetic acid from biomass or from a biomass fraction, including by catalytic, thermochemical and biological means, and that the limited description of various embodiments provided above should by no means be construed as limiting of the ways in which the acetic acid feedstock 12 may be made using renewable resources inclusive fundamentally of biomass, carbon monoxide and carbon dioxide gases. For example, as is known, the required acetic acid may be made at least in some part by anaerobic fermentation using carbon monoxide and carbon dioxide gases themselves for a carbon source.

The present invention is further illustrated by the following example:

EXAMPLE 1

Commercial zirconium hydroxide was dried at 120 degrees Celsius for more than 5 hours. A calculated amount of $Zn(NO_3)_2$ (from Sigma-Aldrich, more than 99.8 percent purity) was dissolved in water, forming a clear solution. The dried zirconium hydroxide (which was also from Sigma-Aldrich, more than 99.8 percent purity) was then mixed with the solution by incipient wetness, in order to form wet powders impregnated with Zn. The wetted powder was then dried at 80 degrees Celsius for 4 hours, followed by calcination at 550 degrees Celsius for 3 hours, to obtain a $Zn_1Zr_8O_z$ catalyst of the type described in the '433 application (though for converting ethanol to isobutene) by an incipient wetness impregnation method.

An acetic acid to isobutene process was conducted with the catalyst thus prepared in a fixed-bed stainless steel reactor having an inside diameter of 5 millimeters. 100 mg of the catalyst was packed between quartz wool beds. A thermocouple was placed in the middle of the catalyst bed to monitor the reaction temperature. Before beginning the reaction, the catalyst bed was pretreated by flowing 50 ml/minute of nitrogen at 450 degrees Celsius through the catalyst over a half hour. A 25 weight percent solution of acetic acid in water was then introduced into an evaporator at 180 degrees Celsius by means of a syringe pump, and the vaporized steam/acetic acid was carried into the reactor by a flowing nitrogen carrier gas at an acetic acid concentration in the gas phase of 1.36 weight percent and a WHSV of 0.1 grams of acetic acid per gram of catalyst per hour. Meanwhile, the product line was heated to in excess of 150 degrees Celsius before a cold trap, to avoid condensing the liquid products in the product line. A reaction temperature of 415 degrees Celsius was employed.

A Shimadzu 2400 gas chromatograph equipped with an auto sampling valve, HP-Plot Q column (30 m, 0.53 mm, 40 μm) and flame ionization detector was connected to the line between the reactor outlet and cold trap to collect and analyze the products in the effluent gas. After the cold trap, an online micro-GC (MicroGC 3000A equipped with molecular sieves 5A, plot U columns and thermal conductivity detectors) was used to analyze the product gases specifically, using nitrogen as a reference gas.

Figure 2:
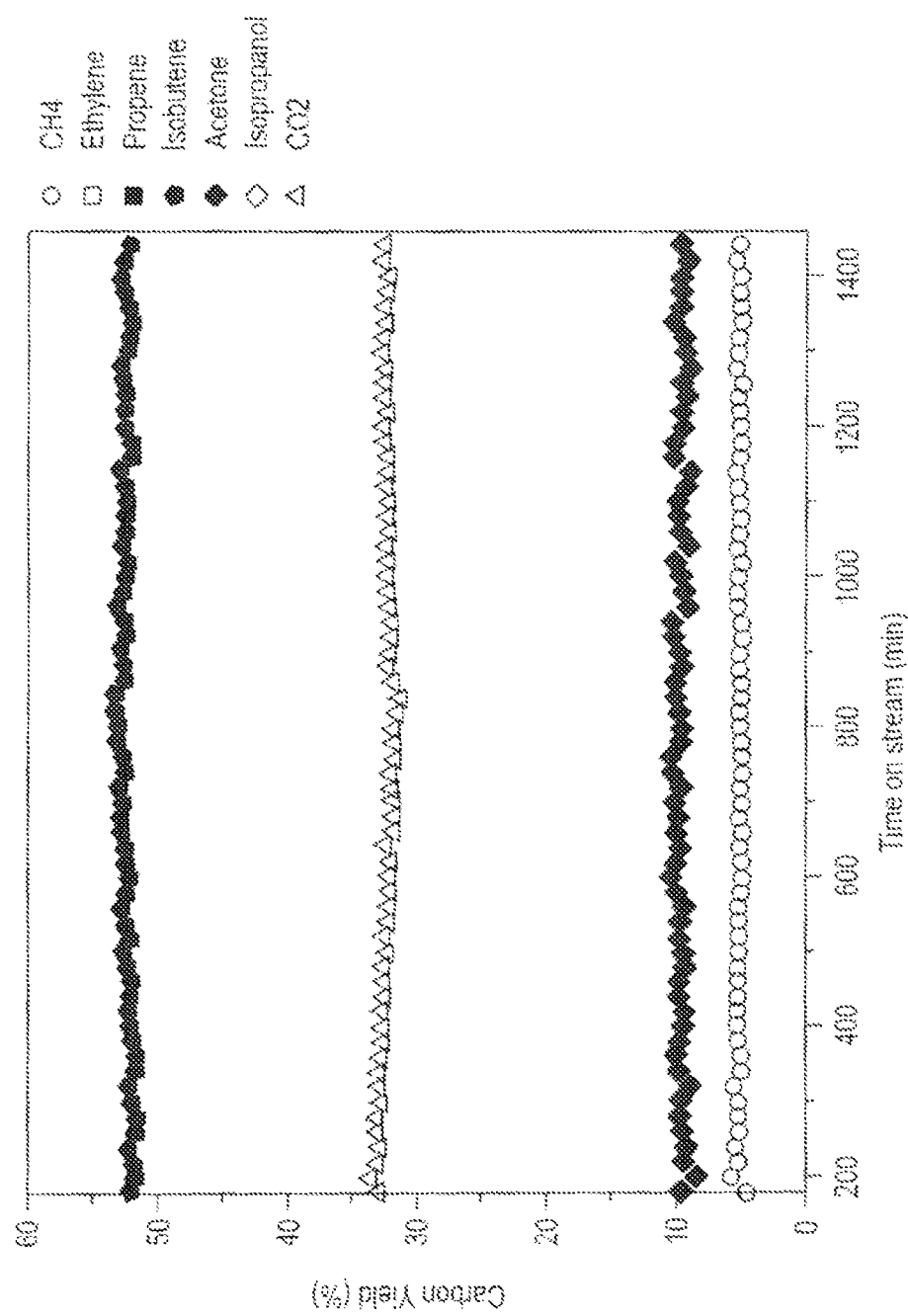
FIG. 2 shows the yields of the various products in a process according to the present invention over time, carried out as described in Example 1 below.

FIG. 2 shows the results of a one-pass durability test of the $Zn_1Zr_8O_z$ catalyst prepared by the incipient wetness impregnation method, in converting acetic acid to isobutene in a gas phase process as described. A consistent product of about 5 percent by weight of methane, about 10 percent by weight of acetone, about 33 percent by weight of carbon dioxide and more than about 50 percent by weight of the desired isobutene product was obtained; in contrast to the ethanol to isobutene process using these same $Zn_xZr_yO_z$ mixed oxide catalysts, no ethylene or propylene was produced. The catalyst showed very high stability over the full duration of the run, with no signs of observable deactivation after more than 1400 minutes of time-on-stream operation.

EXAMPLES 2 THROUGH 10

For these examples, additional $Zn_xZr_yO_z$ mixed oxide catalysts were prepared both by the incipient wetness method used in Example 1 (IW in Table 1 below) but also by the prior art hard template method (HT), and these were evaluated and the products analyzed using the same apparatus and method described in Example 1 but under different sets of reaction conditions (as summarized in Table 1 below).

TABLE 1

Further Acetic acid to Isobutene Examples

| Ex # | Catalyst | Zn/Zr ratio | Reaction temp. (° C.) | WHSV ($g_{acetic}$/$g_{catal}$/hr) | Steam to carbon ratio | $C_{G\text{-}acetic\ acid}$ (wt %) | Acetone selectivity (mol %) | Isobutene selectivity (mol %) |
|---|---|---|---|---|---|---|---|---|
| 2 | HT | 1/15 | 450 | 0.25 | 5 | 1.3 | 30.5 | 41.7 |
| 3 | HT | 1/15 | 450 | 1.14 | 5 | 1.5 | 61.1 | 18.4 |
| 4 | IW | 1/8  | 415 | 0.1  | 5 | 1.4 | 9.8 | 52.5 |
| 5 | IW | 1/10 | 415 | 0.95 | 5 | 22.3 | 50.8 | 20.1 |
| 6 | IW | 1/10 | 450 | 0.16 | 2.5 | 18.8 | 0.7 | 50.6 |
| 7 | IW | 1/10 | 450 | 0.65 | 2.5 | 18.8 | 8.3 | 46.9 |
| 8 | IW | 1/10 | 415 | 0.16 | 2.5 | 18.8 | 5.7 | 57.2 |
| 9 | IW | 1/10 | 415 | 0.33 | 2.5 | 18.8 | 16.4 | 45.3 |
| 10 | IW | 1/10 | 415 | 0.65 | 2.5 | 18.8 | 30.5 | 35.0 |

The invention claimed is:

1. A process for converting acetic acid to isobutene comprising: contacting acetic acid with a $Zn_xZr_yO_z$ mixed oxide catalyst in which the ratio of x:y is from 1:100 to 10:1 and z is a stoichiometric coefficient for the $Zn_xZr_yO_z$ mixed oxide catalyst to produce a product mixture including isobutene, and recovering isobutene from the product mixture.

2. The process according to claim 1, wherein the $Zn_xZr_yO_z$ mixed oxide catalyst contains less than 0.14 percent by weight of sulfur.

3. The process according to claim 2, wherein the $Zn_xZr_yO_z$ mixed oxide catalyst contains less than 0.01 percent by weight of sulfur.

4. The process according to claim 3, wherein the $Zn_xZr_yO_z$ mixed oxide catalyst contains less than 0.001 percent by weight of sulfur.

5. The process according to claim 1, wherein x:y is from 1:30 to 1:1.

6. The process according to claim 5, wherein x:y is from 1:20 to 1:5.

7. The process according to claim 6, wherein x:y is from 1:12 to 1:10.

8. The process according to any one of claims 1, 2, 3 or 4, conducted continuously in the gas phase by vaporizing acetic acid or an acetic acid solution in water to produce a vaporized acetic acid or a vaporized acetic acid and steam mixture and then bringing the vaporized acetic acid or the vaporized acetic acid and steam mixture into contact with the $Zn_xZr_yO_z$ mixed oxide catalyst under reaction conditions which are effective for converting the acetic acid to isobutene.

9. The process according to claim 8, wherein acetic acid is supplied to the $Zn_xZr_yO_z$ mixed oxide catalyst at a steam to carbon ratio of from 0 to 20 and a weight hourly space velocity of from 0.01 hr$^{-1}$ to 10 hr$^{-1}$, and is converted to isobutene at a reaction temperature from 350 to 700 degrees Celsius.

10. The process according to claim 9, wherein acetic acid is supplied at a steam to carbon ratio of from 2 to 5 and a weight hourly space velocity of from 0.05 hr$^{-1}$ to 2 hr$^{-1}$, and is converted to isobutene at a reaction temperature of from 400 to 500 degrees Celsius.

11. The process according to claim 1, wherein the acetic acid is obtained at least in part by fermentation of one or more of the five- and six-carbon sugars.

12. The process according to claim 1, wherein the acetic acid is obtained at least in part through an oxidative fermentation from ethanol.

13. The process according to claim 1, wherein the acetic acid is obtained at least in part by carbonylation of methanol.

14. The process according to claim 13, wherein the methanol is obtained at least in part by combining carbon dioxide generated from biomass and hydrogen under conditions which are effective for forming methanol.

\* \* \* \* \*